United States Patent [19]

Hillsman et al.

[11] 4,036,221
[45] July 19, 1977

[54] RESPIRATOR

[75] Inventors: Deane Hillsman; Albert M. Cook; James G. Simes, all of Sacramento, Calif.

[73] Assignee: Sutter Hospitals Medical Research Foundation, Sacramento, Calif.

[21] Appl. No.: 564,336

[22] Filed: Apr. 2, 1975

Related U.S. Application Data

[63] Continuation-in-part of Ser. No. 490,183, July 19, 1974, abandoned, which is a continuation of Ser. No. 249,380, May 1, 1972, abandoned.

[51] Int. Cl.² .................................................. A61M 16/00
[52] U.S. Cl. .......................... 128/145.6; 128/DIG. 17
[58] Field of Search ....................... 128/145.5–145.8, 128/188, 142–142.3, DIG. 17, DIG. 29, 30.2; 137/102, 87, 88; 73/198, 279, 274

[56] References Cited

U.S. PATENT DOCUMENTS

| | | | |
|---|---|---|---|
| 2,946,330 | 7/1960 | Blair | 128/29 |
| 3,033,195 | 5/1962 | Gilroy et al. | 128/145.8 |
| 3,714,941 | 2/1973 | Kipling | 128/188 |
| 3,729,000 | 4/1973 | Bell | 128/145.6 |
| 3,741,208 | 6/1973 | Jonsson et al. | 128/145.6 |
| 3,840,006 | 10/1974 | Buck et al. | 128/145.8 |
| 3,863,082 | 1/1975 | Gillott et al. | 128/145.6 |
| 3,905,362 | 9/1975 | Eyrick et al. | 128/145.6 |

Primary Examiner—Robert W. Michell
Assistant Examiner—Henry J. Recla
Attorney, Agent, or Firm—Christie, Parker & Hale

[57] ABSTRACT

A volume-cycled respirator including a piston driven by a translational motor in a feedback control system for forcing a controlled volume of gas into the lungs of a patient throughout each inspiratory cycle. A waveform generator produces a volume-versus-time waveform representing the desired volume of gas to be delivered to the patient throughout each inspiratory cycle. The feedback loop includes a position transducer responsive to the changing position of the piston for producing a volume-versus-time waveform representing the actual volume of gas delivered to the patient throughout each inspiratory cycle. The desired waveform is compared with the actual waveform to produce an error signal which drives the translational motor so it forces the piston travel waveform to follow the desired waveform.

29 Claims, 27 Drawing Figures

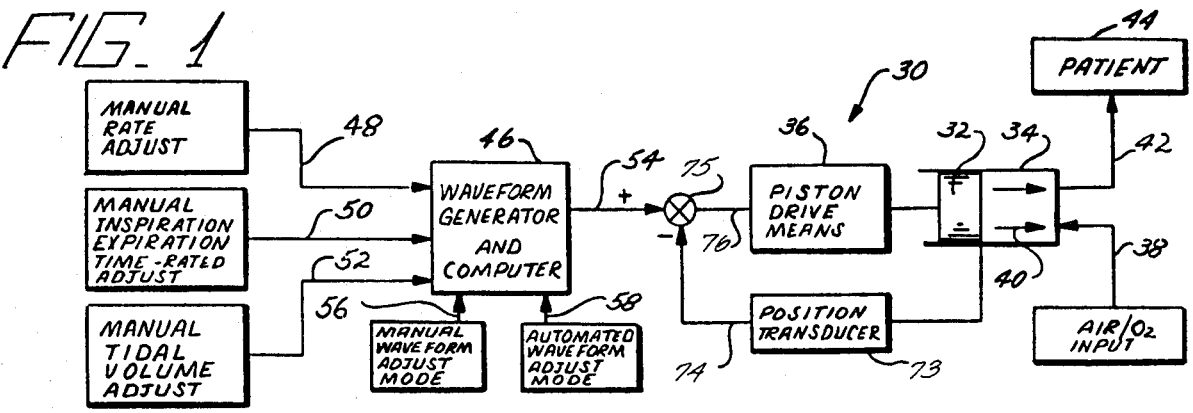
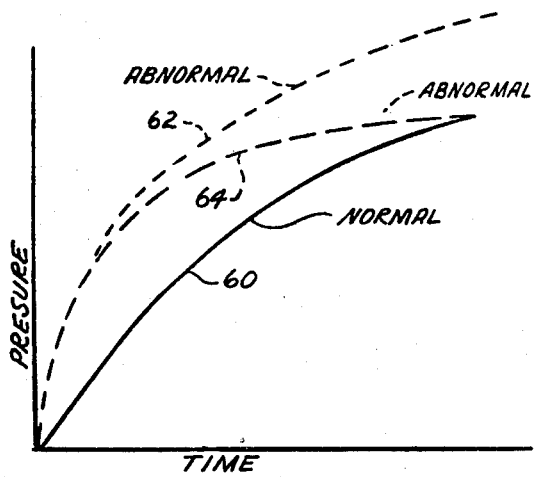
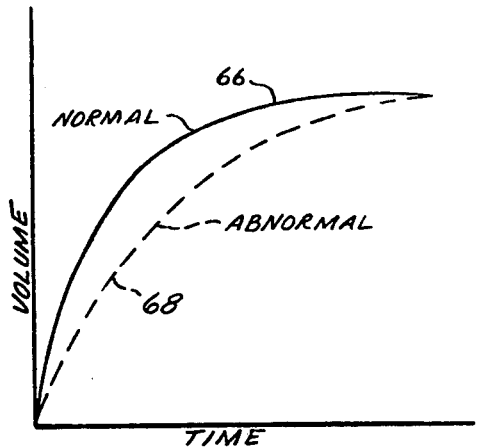
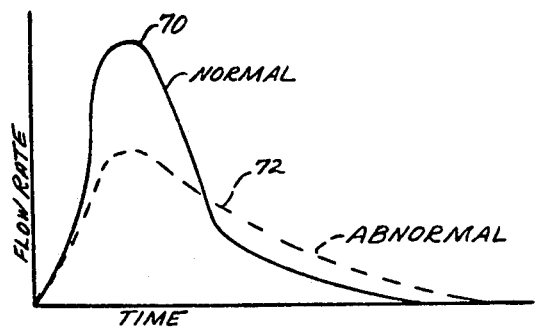

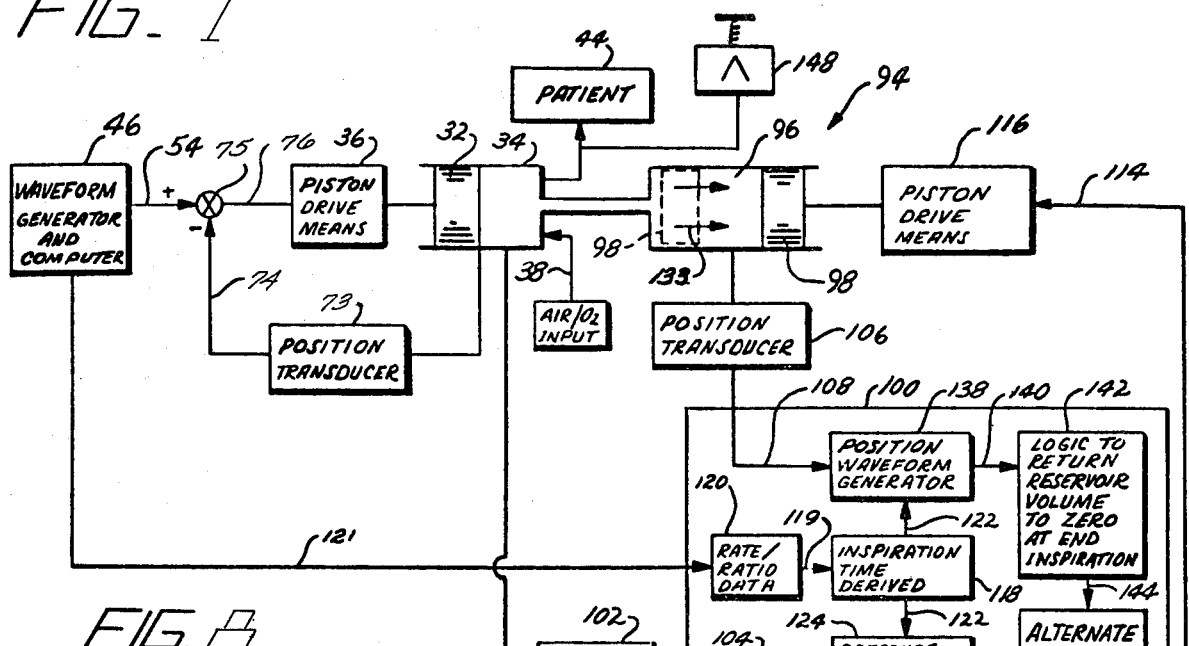
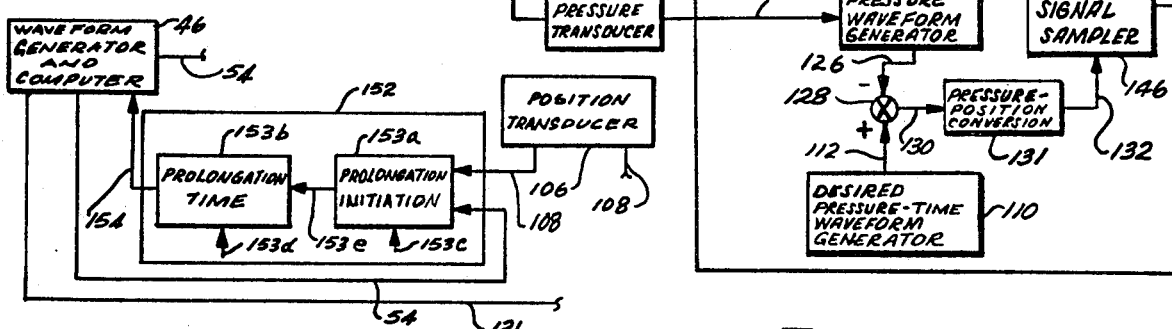
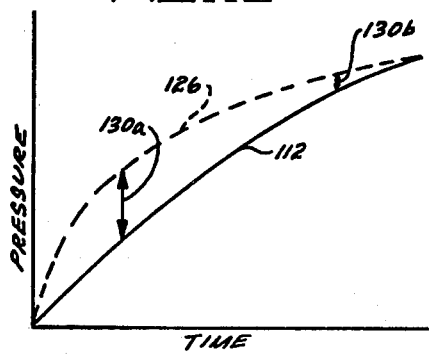
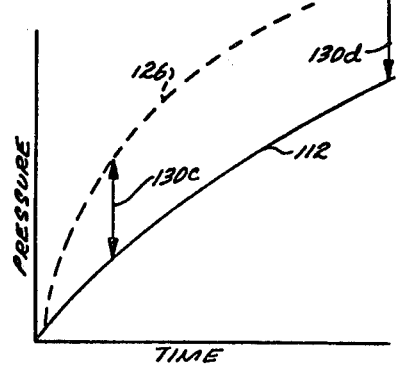
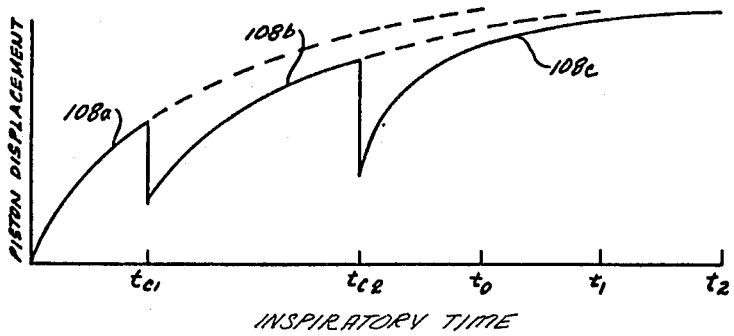

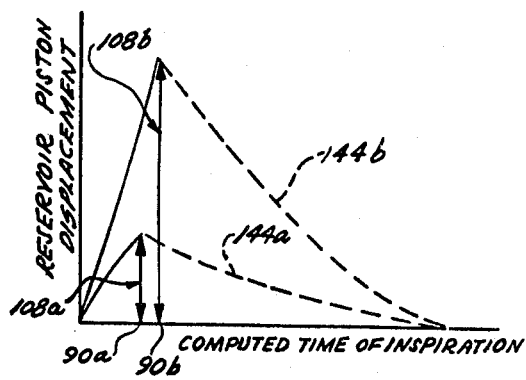
FIG_12
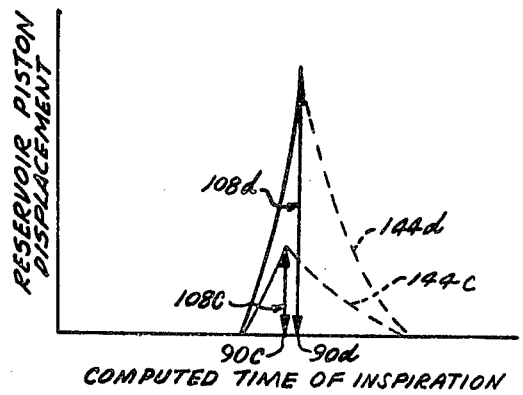
FIG_13
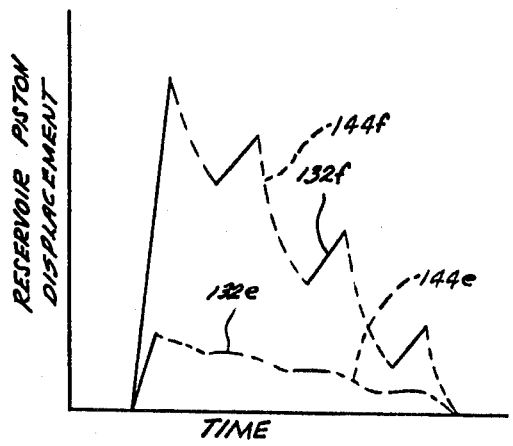
FIG_14
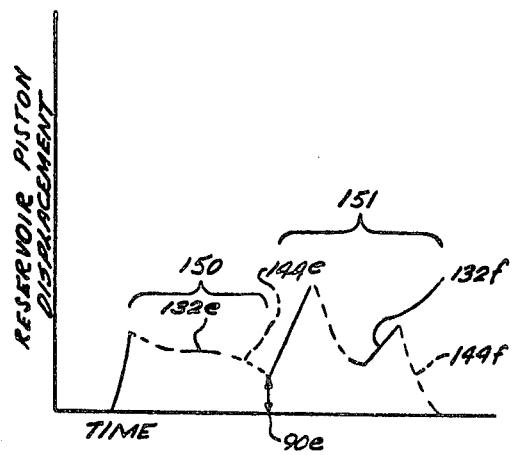
FIG_15
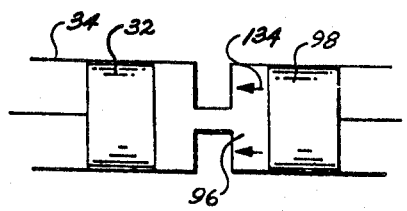
FIG_16
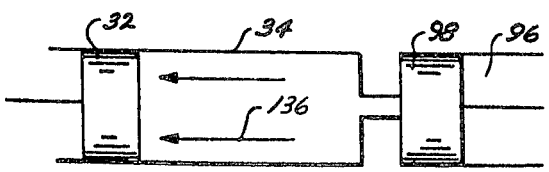
FIG_17

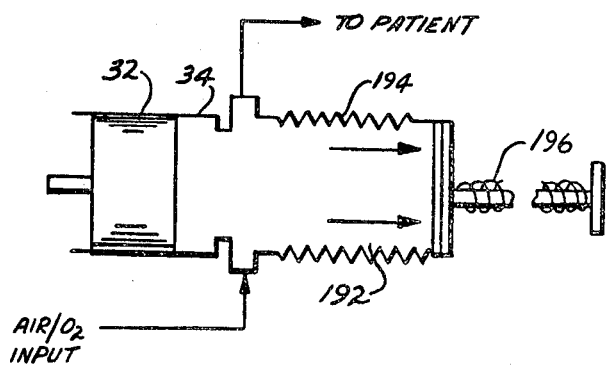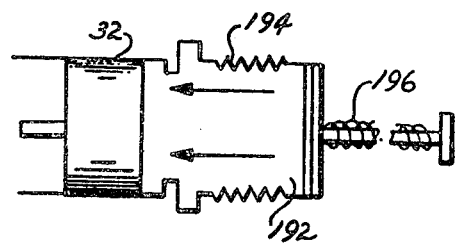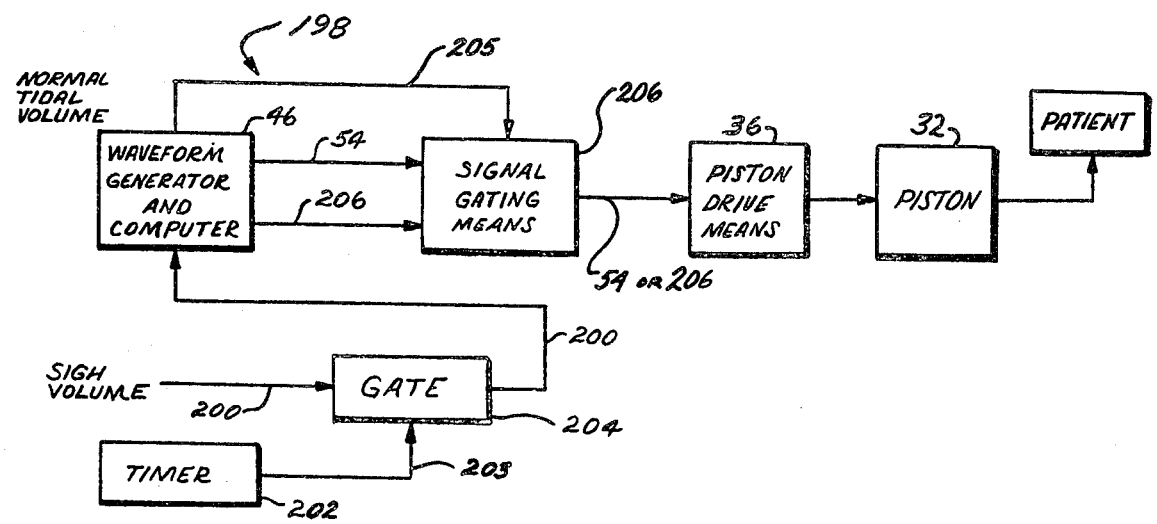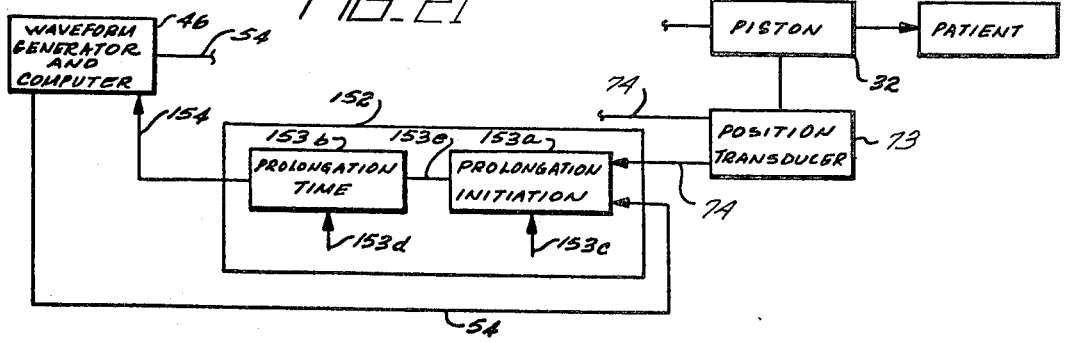

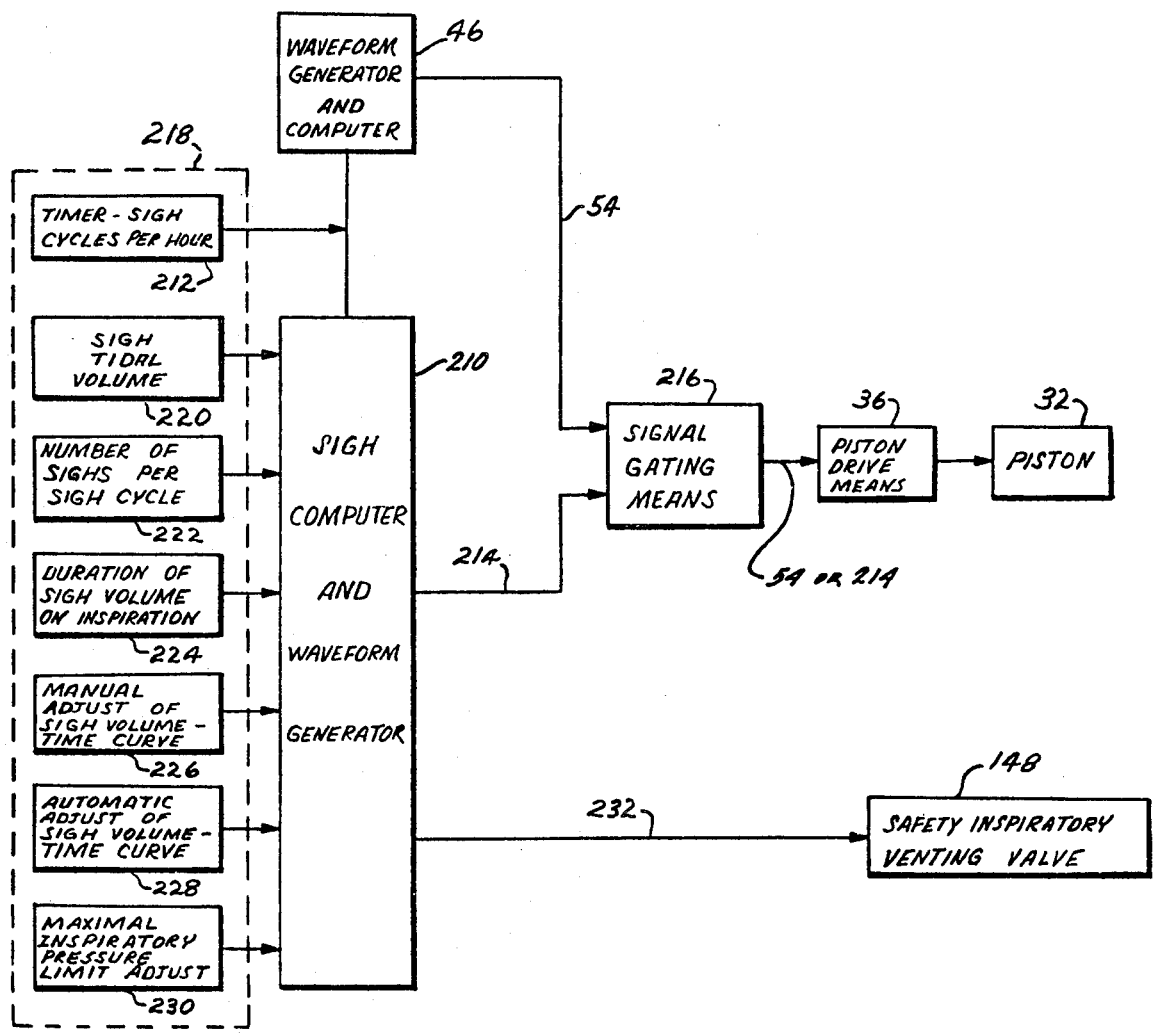

RESPIRATOR

CROSS-REFERENCE TO RELATED APPLICATIONS

This is a continuation-in-part of our application Ser. No. 490,183, filed July 19, 1974 now abandoned which, in turn, is a continuation of our application Ser. No. 249,380, filed May 1, 1972 now abandoned.

FIELD OF THE INVENTION

This invention relates to respirators, and more particularly to a volume-cycled respirator for delivering gas to patients under controlled conditions considering the specific pathological problem of each patient's pulmonary system.

PRIOR ART

This invention represents an improvement over the respiratory systems disclosed in the following patents:

| U.S. Patent No. | Inventor |
| --- | --- |
| 3,729,000 | Bell |
| 3,741,208 | Jonsson et al |
| 3,768,468 | Cox |

BACKGROUND OF THE INVENTION

A respirator forces gas into the lungs of a patient who is incapable of breathing normally for himself. Generally speaking, normal breathing is impaired either because of pathological problems with the patient's lungs, such as high airway resistance or lung stiffness, or because of other extra-pulmonary physiological problems, such as paralysis due to poliomyelitis, head injuries, and the like, which prevent the patient from obtaining adequate ventilation.

Prior art volume-cycled respirators ordinarily contain adjustments for the number of times per minute gas is forced into the patient's lungs and for the volume of gas delivered during a cycle. However, such prior art respirators do not adequately control the volume of gas delivered as a function of time throughout each inspiratory cycle to provide a timerelated volume-flow profile which is best suited for each patient in view of his specific pathological breathing problem. For example, prior art respirators lack precise controls for optimizing the inspiratory breath and achieving maximum possible gas distribution within the lung without undesirable premature airway pressure buildup.

Thus, there is a chance that excessive pressure can build up in the lungs of a respirator patient suffering from high airway resistance or lung stiffness problems. This could injure the patient's lungs, or cause extreme discomfort while he is using the respirator. To solve this problem, prior art respirators generally have used a relief valve for "aborting the cycle", i.e., immediately venting gas in the respirator to the room air when excessive pressure buildup is sensed. However, this procedure has the disadvantage of wasting gas which should be delivered to the patient to maintain proper ventilation.

Several known respirator systems have attempted to provide more precise controls over the air delivered to the patient. Many such respirators use "open loop" control over the respirator cycling. Typical open loop systems are described in the patents to Bell and Cox referred to above. In these systems the volume of gas delivered to the patient is measured during each cycle. When the actual volume reaches some desired fixed volume, the inspiration cycle is automatically stopped.

The patent to Jonsson et al. referred to above discloses a closed loop system for controlling respiratory cycling. The Jonsson et al. system produces a reference signal which defines a desired time-dependent flow rate of gas to be delivered to the patient. The reference signal is fed to a servo unit which includes a flow meter for generating a signal representing the actual flow rate of gas being delivered to the patient. The reference flow rate signal and the signal from the flow meter are compared to generate an error signal which controls a mechanical flow control unit which pinches down or backs off on a conduit extending from a bellows to the patient to control the flow rate of gas to the patient.

SUMMARY OF THE INVENTION

This invention provides a volume-cycled respirator system which controls the flow of gas to a patient's lungs so that the manner in which the gas is delivered to the patient from the beginning to the end of each inspiratory cycle can be precisely controlled according to the patient's specific pathological breathing problem.

Briefly, the respirator system includes gas delivery means which are displaceable for periodically forcing a volume of gas under pressure into the lungs of a patient during an inspiratory period of a respiratory cycle. Drive means connected to the gas delivery means displace the volume of gas to be delivered. A reference signal is generated to represent the time-varying position of the gas delivery means necessary to deliver a desired inspiratory volume of gas in accordance with a desired volume-versus-time waveform. Closed loop feedback means continuously control changes in the position of the gas delivery means throughout the inspiratory period to deliver gas to the patient in accordance with the desired waveform. The feedback loop includes means which are responsive to the actual position of the gas delivery means for generating a position feedback signal representing the actual volume-versus-time waveform of gas delivered to the patient. In response to the reference signal and the position feedback signal, an error signal is generated and applied to the drive means to control the position of the gas delivery means throughout the inspiratory period.

In a preferred form of the invention, the gas delivery means includes a piston movable in a cylinder for delivering gas to the patient. The piston preferably is driven by a translational motor, such as a linear d.c. permanent magnet motor. A position transducer, preferably a linear variable-differential transformer, provides an output proportional to the position of the piston as it moves in response to the translational motor.

Preferably, the desired volume-versus-time waveform is an idealized time-flow of gas to be delivered throughout each inspiratory cycle considering the specific pathological characteristics of the patient's pulmonary system. For example, a cardiac patient will require a gas flow waveform which is different from that of an emphysema patient. The desired volume-versus-time waveform can be a fixed waveform, but preferably the waveform can be adjusted during the inspiratory cycle to accommodate certain pathologic circumstances which may develop during the cycle. For example, gas pressure buildup during inspiration can be monitored. If the monitored gas pressure buildup becomes excessive, such as when the patient has difficulty accepting the gas because of either high airway resistance problems and/or lung stiffness problems (from emphysema and/or pulmonary fibrosis, for example), the control system can accommodate the excessive pressure buildup without aborting the inspiratory cycle. Thus, the desired volume of gas will ultimately be forced into the patient's lungs by the end of the inspiratory cycle, rather than being wasted by being vented to the room air.

The respirator system of this invention provides an improvement over open loop systems such as those shown in the patents to Bell and Cox, referred to above. These open loop systems lack the ability to control gas flow to the patient in accordance with a desired time-varying waveform throughout the inspiratory cycle. Thus, the precise control of the gas flow waveform, which is important if the patient is a cardiac patient of has emphysema, is lacking in these respirators. In addition, the actual air flow waveform of these respirators is highly dependent upon such parameters as airway resistance, lung compliance, and even changes in the respirator system itself.

The respirator system of the present invention also is less complex than the closed loop system disclosed in the Jonsson et al. patent referred to above. one disadvantage of the Jonsson et al. respirator is its dependence upon flow rate, which is a very difficult parameter to either measure or control. On the other hand, the respirator system of this invention controls the volume waveform by a position feedback system. Position transducers are much simpler than transducers which sense flow rate. Flow rate transducers are inherently unstable and therefore not accurate. The problems with using flow rate transducers are compounded further when used in closed loop feedback systems in which any variations in the transducer output drastically affect the operation of the system. For example, the Jonsson et al. system requires additional power-consuming and costly zero-shift comparators, linearizers, and integraters to stabilize the closed loop system.

A further advantage of the respirator system is gained by the use of a translational d.c. motor for driving the respirator piston. The translational motor provides the capability of simply yet accurately controlling the instantaneous position of the piston throughout the inspiratory cycle. To control the volume waveform in a respirator driven by a rotary motor would require a complicated gear train assembly and connecting rods between the rotary output shaft of the motor and the linearly-driven piston in the respirator. This would be required to provide adjustments in the approximately sinosoidal motion of the piston being driven by a rotary motor and its associated connecting rod and crankshaft. Due to the accurate control over piston travel provided by the present invention, variable pressure limiting can be provided by the respirator control system without aborting the respiratory cycle.

Thus, the travel of the respirator piston can be adjusted during each inspiration cycle to assure delivery of a predetermined volume of gas to the patient by the end of the cycle. If there are pathological problems associated with the patient's lungs, or coughing, or voluntary patient resistance to the respirator's effort, excessive pressure buildup in the patient's lungs during the early portion of the inspiratory cycle can be prevented, and a portion of the necessary volume of gas is not lost through the standard safety relief valve, but can be delivered to the patient during the later portion of the cycle. Thus, the system maximizes the chance that the entire predetermined volume of gas will be delivered to the patient before the end of the inspiratory cycle. This avoids the problem of having the air vented to the surrounding air, which deprives the patient of air necessary for proper ventilation.

These and other aspects of the invention will be more fully understood by referring to the following detailed description and the accompanying drawings.

BRIEF DESCRIPTION OF THE DRAWINGS

FIG. 1 is a schematic block diagram showing a respirator system which includes a linearly-driven piston in a position feedback control system;

FIG. 2 is a graph showing a waveform representing idealized time-varying pressure of gas in a normal patient throughout an inspiratory cycle as compared with a pair of waveforms representing gas pressure in abnormal patients with common types of abnormal pressure buildup;

FIG. 3 is a graph showing a waveform representing an idealized time-varying volume of gas delivered to a normal patient throughout an inspiratory cycle as compared with a waveform representing the volume of gas delivered to an abnormal patient;

FIG. 4 is a graph showing a waveform representing an idealized time-varying flow rate of gas delivered to a normal patient throughout an inspiratory cycle as compared with a waveform representing the flow rate of gas delivered to an abnormal patient;

FIG. 7 is a schematic block diagram showing a system for controlling the flow of gas to a patient from a respirator having an accommodation reservoir and a system for controlling the volume of gas in the accommodating reservoir;

FIG. 8 is a schematic block diagram showing the system of FIG. 7 modified to include an inspiratory prolongation override system;

FIG. 9 is a graph showing a waveform representing piston displacement in response to the prolongation override system shown in FIG. 8;

FIG. 10 is a graph showing a time-dependent buildup of pressure for an abnormal patient using the respirator system of FIG. 7, in which the pressure buildup is being accommodated by the pressure accommodating system, and in which the accommodated pressure buildup is compared with an idealized pressure buildup for a normal patient;

FIG. 11 is a graph showing a time-dependent buildup of pressure for an abnormal patient using the respirator system of FIG. 7, in which the pressure buildup is not accommodated by the pressure accommodation system, and in which the pressure buildup in the system is compared with an idealized pressure buildup for a normal patient;

FIG. 12 is a graph representing the volume displacement of the accommodating piston in the pressure accommodation system of FIG. 7, in which both large and small volume displacements occurring early in respiration are respectively returned to a programmed zero volume by the end of the inspiratory cycle;

FIG. 13 is a graph representing the volume displacement of the accommodating piston in the pressure accommodation system of FIG. 7, in which both large and small volume displacements occurring late in respiration are respectively returned to a programmed zero volume by the end of the inspiratory cycle;

FIG. 14 is a graph comparing composite volume displacements of the pressure accommodation system of FIG. 7 for two patients, one curve describing adequate pressure accommodation with a progressive return of the accommodating reservoir volume to zero, the other curve describing inadequate pressure accommodation, but with a similar progressive return of the reservoir to zero volume by the end of inspiration;

FIG. 15 is a graph showing a composite volume displacement of the pressure accommodation system of FIG. 7, in which adequate pressure accommodation occurs early in inspiration, and inadequate pressure accommodation occurs later in inspiration, but in which the reservoir volume is progressively returned to zero by the end of the inspiratory cycle;

FIG. 16 is a schematic elevation view showing the respirator system of FIG. 7 during a late portion of the inspiratory cycle, in which the accommodating reservoir accommodates a premature pressure buildup and in which resistive emptying force of the reservoir has occurred;

FIG. 17 is a schematic elevation view showing the respirator system of FIG. 7 during the expiratory cycle with return of the accommodation reservoir to zero volume;

FIG. 21 is a schematic block diagram showing a method of modifying the system of FIG. 19 to include an inspiratory prolongation override system;

FIG. 22 is a schematic diagram showing an alternate embodiment of the accommodating reservoir during an early portion of the inspiratory cycle, in which reservoir accommodation has occurred;

FIG. 23 is a schematic diagram of the accommodating reservoir of FIG. 22 during a late portion of the inspriatory cycle, in which reservoir emptying has occurred;

FIG. 24 is a schematic block diagram showing means for providing a periodic artificial sigh during inspiration;

FIG. 25 is a graph showing a volume-time relationship of normally-generated inspiratory breaths, in which the volume-time relationship is overridden by the artificial sigh system shown in FIG. 24;

FIG. 26 is a schematic block diagram of an alternate embodiment of the artificial sigh system shown in FIG. 24; and FIG. 27 is a graph showing a volume-time relationship of inspiratory breaths generated by the artificial sigh system shown in FIG. 26.

DETAILED DESCRIPTION OF THE PREFERRED EMBODIMENTS

Figure 5:
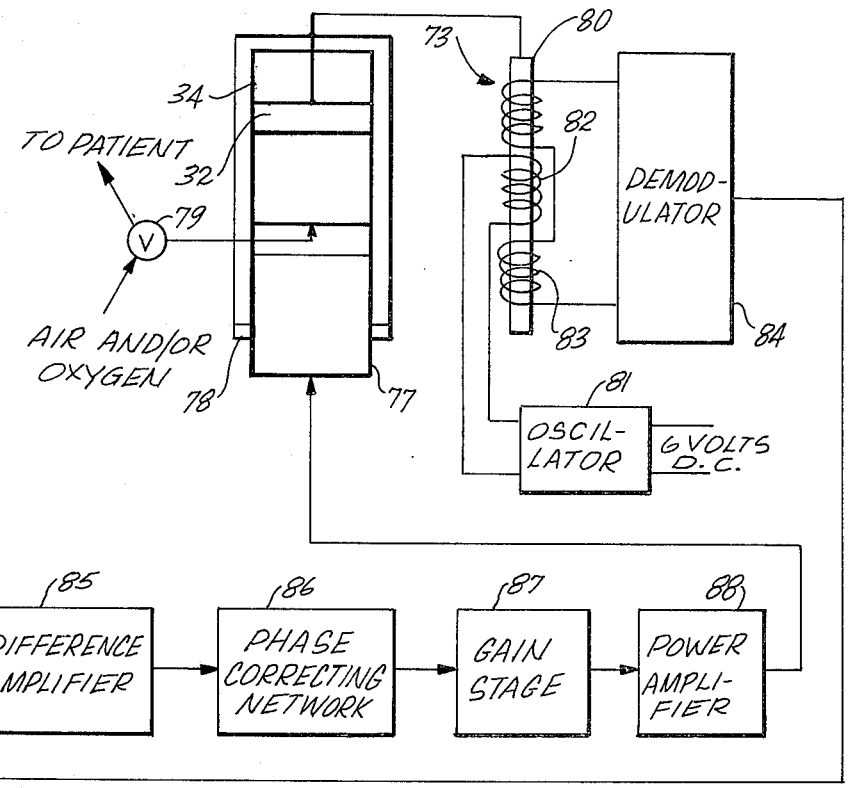
FIG. 5 is a schematic block diagram showing a preferred embodiment of a position feedback control system for controlling the position of a respirator piston.

Referring to FIG. 1, a respirator 30 includes a piston 32 disposed in a cylinder 34. The piston is driven back and forth in the cylinder by suitable drive means 36, preferably a translational motor coupled to the piston by suitable means. The preferred translational motor is a permanent magnet motor of the type disclosed in U.S. Pat. No. 3,863,082 which is assigned to the assignee of this application. However, other translational motors such as a linear actuator, or a linear induction motor can be used without departure from the scope of the invention.

A line 38 delivers a supply of gas, usually air or a suitable mixture of air and oxygen, to the interior of the piston cylinder. When the piston drive means 36 forces the piston in the direction of the arrow 40 in FIG. 1, gas admitted through the line 38 is forced out of piston cylinder 34 by suitable valves (not shown) through a line 42 connected to a patient (represented schematically at 44) in a conventional manner to deliver the gas to the patient's lungs. The reciprocating movement of the piston periodically pumps the gas into the patient's lungs to simulate the inspiratory cycle of normal breathing and allow suitably adjusted time for expiration. The expiratory cycle occurs each time the piston is retracted, with the patient exhaling passively through a separate conduit (not shown), or with expiratory assistive devices or retard devices (not shown) as is well known in the art of respirator therapy.

This invention provides means for controlling the position of the respirator piston to deliver a controlled volume of gas to the patient throughout each inspiratory cycle in accordance with a desired volume-versus-time waveform. A computer and waveform generator 46 receives input data which establish the time-related volume of gas to be delivered during each inspiration cycle. Such input data include an adjustable respiratory rate (breath per minute) command 48, an adjustable inspiration/expiration time ratio command 50, and an adjustable tidal volume command 52.

Waveform generator 46 preferably is a digital signal generator with a digital clock disclosed in application Ser. No. 461,303, filed Apr. 16, 1974. However, other signal generators, such as a special purpose analog computer, may be used without departing from the scope of the invention. The waveform generator responds input data to produce a reference output or waveform 54 proportional to the desired volume of gas to be delivered to the patient as a function of inspiration time. Preferably, output 54 is a position waveform which causes the piston to travel so it forces a desired time-related volume of gas into the lungs of the patient throughout the inspiratory cycle. In a preferred form of the invention, output 54 can be adjusted manually by an operator to generate a desired waveform input signal 56, or it can be automatically adjusted, as illustrated schematically, by an input signal 58 representing a desired waveform generated internally within the waveform generator. For example, the operator can select a particular waveform representing the time-dependent volume of gas which is best accommodated considering the patient's particular breathing condition. Thus, waveforms representing normal patients, or patients with mild airway obstruction, severe airway obstruction, decreased pulmonary compliance, or the like can be chosen. Although reference output 54 preferably defines an optimal time-related volume of gas, a time-related pressure function, or a time-related flow rate function, may be produced to achieve the same purpose, which is to drive the respirator piston so it delivers gas to the patient under idealized conditions, taking into account the specific pathological problem of the patient's pulmonary system.

The idealized time-volume function produced by the waveform generator may be for normal conditions, i.e., for a patient whose lungs are not diseased, but who is temporarily incapable of breathing normally for himself, or for abnormal patients having such conditions as high airway resistance (such as asthma or emphysema) or low pulmonary compliance (lung stiffness, such as pulmonary fibrosis).

FIGS. 2 through 4 show curves which describe the pulmonary dynamics of a normal patient compared with that of abnormal patients. A curve 60 in FIG. 2 represents a typical pressure build-up in the lungs of a normal patient during inspiration. A pair of curves 62 and 64 in FIG. 2 represent two common types of pressure build-up in the lungs of abnormal patients whose resistance or compliance problems cause pressure to build up at a faster rate during the early portion of the inspiratory cycle when compared with that of the normal patient. When a respirator forces gas into the lungs of a patient, care must be taken to prevent the build-up of excessive pressure because each pressure could injure the patient's lungs, such as by rupturing. It is also desirable to deliver a predetermined fixed volume of gas to each given patient during each inspiratory cycle. Prior art respirators often have the disadvantage of allowing excessive pressure to build up in abnormal patient situations when a predetermined necessary volume of gas is delivered to them, which triggers a releif valve and vents the gas to the atmosphere, thereby wasting the gas which is necessary for proper ventilation.

The respirator of this invention drives the respirator piston 32 so that gas is delivered under conditions which substantially prevent excessive pressure build-up in abnormal patients (as represented by curves 62 or 64), and maximize the chance that the necessary desired volume of gas will be delivered to the patient by the end of each cycle. As will. become clear from the following detailed description, the respirator of this invention produces an optimal distribution of gas within the lung, while minimizing the change of venting necessary gas to the atmosphere.

As described above, the idealized pressure build-up during inspiration preferably is provided by controlling the volume of gas delivered to the patient throughout each inspiratory cycle. A volume-versus-time curve 66 in FIG. 3 shows how the lungs of a normal patient fill when a predetermined volume of gas is forced into them. A curve 68 in FIG. 3 represents a volume-time relationship for an abnormal patient, in which the initial filling of the patient's lungs is lower than that for the normal patient. However, the rate of filling is greater for the abnormal patient during the later portion of the cycle, and both patients receive the same volume of gas by the end of the inspiratory cycle, unless excess pressure develops in the lungs of the abnormal patient, causing venting of gas to the atmosphere.

The following description will show that the respirator delivers gas under idealized conditions represented generally by the volume-versus-time curve 66. However, for more abnormal patients, the volume-time waveform 54 may be altered, either manually or automatically by inputs 56 or 58, respectively, to conform more to waveform 68, and thereby optimize delivery of gas to a patient having more adverse pulmonary dynamic conditions.

The respirator of this invention alternatively can be adapted to provide an idealized pressure build-up by controlling the flow rate of gas delivered to the patient during each inspiratory cycle. A curve 70 in FIG. 4 shows a flow rate of gas into the lungs of a normal patient. A curve 72 in FIG. 4 illustrates flow rate as a function of time for an abnormal patient in which the initial rate of filling is lower than for the normal patient. However, the terminal flow rate is greater for the abnormal patient, so that the same volume of gas is delivered to both patients by the end of the inspiratory cycle.

Preferably, the position of the piston 32 is accurately controlled by a closed loop position feedback system which continuously adjusts the travel of the piston so it maintains the desired flow of gas represented by the waveform signal 54. The feedback control system includes a transducer 73 for measuring the system's controlled variable, which is preferably the volume of gas actually delivered to the patient as a function of time. Alternatively, transducer 73 measures the volume of gas remaining in cylinder 34. Preferably, the transducer 73 is a position transducer which determines the instantaneous actual position of piston 32 within cylinder 34 and produces a position feedback signal or waveform 74 proportional to the actual volume of gas delivered by piston 32. The feedback control system also includes means represented by a summing point 75 for comparing the desired position signal 54 with position feedback signal 74 to produce a position error signal 76 representing the deviation between the desired volume and actual volume of gas delivered by the piston as a function of inspiration time. The position error signal is fed to the piston drive circuitry to continuously adjust the position of the piston.

Thus, the position feedback system forces the piston travel waveform to follow the desired input waveform so that air delivered to the patient can be precisely controlled. Moreover, optional waveform patterns for both normal and abnormal patients may be generated to precisely control the manner in which air is delivered to normal patients or those with specific pulmonary problems.

FIG. 5 schematically illustrates the presently preferred means for implementing the respirator system shown in FIG. 1. A d.c. translational motor, preferably in the form of a permanent magnet motor 77, includes a sliding coil (not shown for clarity) which moves up and down along an elongated central core in a magnetic field developed by permanent magnets (not shown) disposed within the outer steel shell of the motor. The sliding coil supports a pair of opposed force-distributing ears 78 which extend out through slots in the side of the motor shell. The force-distributing ears 78 are directly coupled to a piston 32 so that vertical reciprocating travel of the coil moves the respirator piston up and down within the cylinder 34. A supply of gas, usually air, or a suitable mixture of air and oxygen, is delivered to the interior of the cylinder through a non-rebreathing valve 79. When the permanent magnet motor pulls the piston downward, the gas is forced out through a port of the cylinder, through the nonrebreathing valve, and then through a line connected to the patient in a conventional manner for delivering the gas to the patient's lungs. The reciprocating movement of the piston periodically pumps the gas into the patient's lungs to replace the inspiratory cycle of normal breathing and allows suitably adjusted time for expiration. The expiratory cycle occurs each time the piston is retracted, and the patient exhales passively through a separate conduit (not shown) as is well known in the art of respirator therapy.

The preferred position transducer 73 comprises a linear variable-differential transformer which includes a movable core 80 which is directly coupled to the piston so that the core 80 follows the piston travel. The linear variable-differential transformer continuously translates position change of the piston into a proportional output voltage so as to monitor the actual air volume delivered by the piston. The linear variable differential transformer operates from a six volt d.c. input connected to an oscillator 81 which, in turn, is connected across the input voltage coil 82 of the transformer. The oscillator converts the d.c. input voltage to an a.c. voltage, and the output coil 83 of the transformer produces a linear a.c. output voltage proportional to the travel of the transformer coil. The a.c. output voltage from the output coil 83 is connected to a demodulator 84 which produces a linear d.c. output voltage which represents the piston travel.

The output voltages from the waveform generator 46 and the demodulator 84 are applied to a compensation circuit and servo amplifier to generate a voltage which drives the piston so as to force the piston travel waveform to follow the desired input waveform. As shown in FIG. 5, the voltages from the waveform generator and the demodulator are applied to a differential amplifier 85, and then to a phase correcting network 86, a gain stage 87, and a power amplifier 88. The output from the power amplifier is then applied to the movable coil of the translational motor 77.

Figure 6:
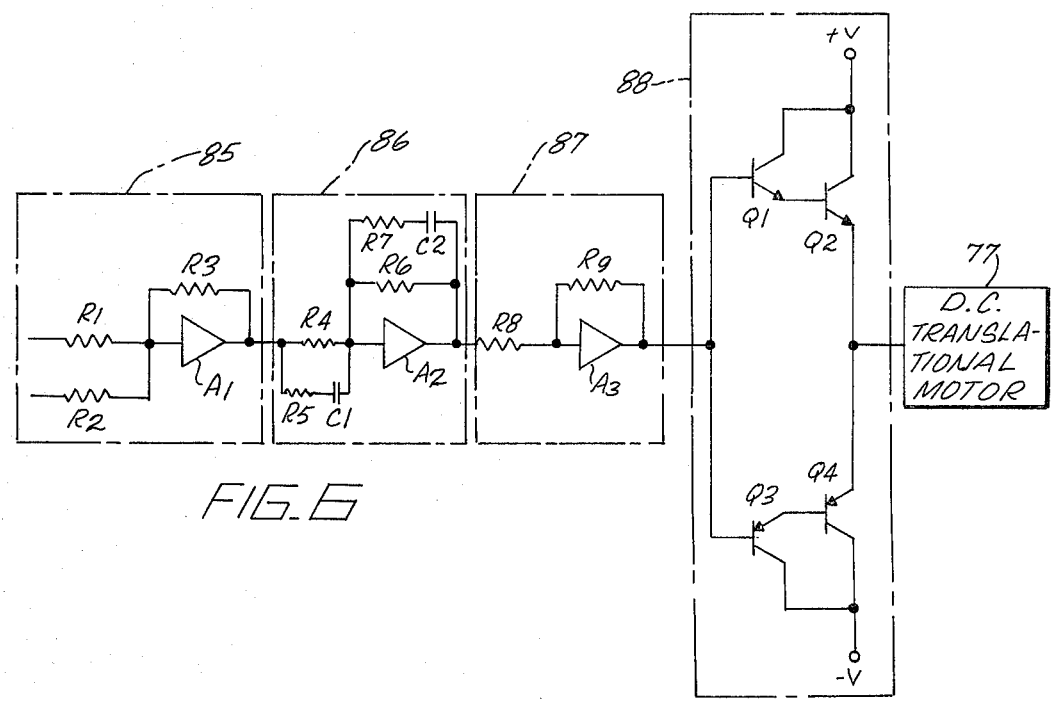
FIG. 6 is a schematic electrical diagram showing the preferred driving circuits for the translational motor for controlling the position of the respirator piston.

The preferred means for implementing the compensation circuit and servo amplifier of FIG. 5 are shown in FIG. 6. The difference amplifier 85 preferably comprises a summing amplifier which includes input resistors $R_1$ and $R_2$. Voltages of opposite polarity from the waveform generator 46 and the demodulator 84 are applied to the input resistors $R_1$ and $R_2$ and then to an amplifier stage $A_1$ which includes a feedback resistor $R_3$. Preferably, the amplifier $A_1$ is the type sold under part No. A 741 manufactured by Fairchild Semiconductor Corp.

The phase correcting network 86 includes an input resistor $R_4$ in parallel with a resistor $R_5$ and capacitor $C_1$. The signal from the difference amplifier is applied across this input network and then to an amplifier stage $A_2$ which includes a feedback resistor $R_6$ in parallel with a resistor $R_7$ and capacitor $C_2$. Preferably, the amplifier $A_2$ is the type sold under the Part No. A 741 sold by Fairchild Semiconductor Corp.

The gain stage 87 preferably includes an input resistor $R_8$ which receives the output voltage from the phase correcting network 86 and then applies it to an amplifier stage $A_3$ having a feedback resistor $R_9$. The amplifier $A_3$ preferably is the type sold under Part No. HC-2000 manufactured by RCA Corp.

The power amplifier 88 preferably comprises a 300 watt push-pull amplifier which includes a first pair of transistors $Q_1$ and $Q_2$ in an emitter-follower configuration and a second pair of transistors $Q_3$ and $Q_4$ also in an emitter-follower configuration. Preferably, the transistors $Q_1$ and $Q_2$ are the type sold under the part No. S-7000 and transistors $Q_3$ and $Q_4$ are the type sold under part Nos. S-7001 manufactured by Motorola Corporation.

Preferably, the power supply voltages for the differential amplifier 85, the phase correcting network 86, the gain stage network 87, and the power amplifier 88 are provided by + 33V, − 28V nickel-cadmium batteries using a continuous battery charger (not shown). The use of the batteries enables the respirator system to serve as an easily portable unit especially adapted for emergencies such as transporting patients or in power outages.

FIG. 7 shows a separate accommodating system 94 which may be used with the basic respirator of FIG. 1 to deliver gas to a patient under conditions which are idealized to compensate for the particular pathological condition of the patient's pulmonary system. The accommodating system includes a secondary or accommodating reservoir 96 in gas communication with cylinder 34 of primary piston 32. Briefly, the accommodating reservoir receives from the primary piston any gas which cannot be accepted because of either high airway resistance or lung compliance problems. Such problems cause premature or inappropriate pressure buildup in the patient's lungs, and gas which cannot be accommodated by the patient because of the pressure buildup is stored in the accommodating reservoir during the early portion of the inspiratory cycle. During the later portion of the inspiratory cycle, the accommodated gas is forced back into the patient's lungs, under controlled and optimized conditions, by a piston 98 in the reservoir. The accommodating system thereby improves the chance that an abnormal patient will be able to pressure-accommodate a certain volume of gas necessary for proper ventilation, instead of venting to the room air any gas which cannot be immediately accepted.

FIG. 7 shows a preferred system for operating the primary and reservoir pistons to deliver gas to the patient under conditions which are controlled depending upon the particular technical pathological problems associated with the patient's pulmonary system. A data processor 100, preferably a special purpose computer, received such input information as instantaneous gas pressure in cylinder 34, and the instantaneous position of reservoir piston 98. Gas pressure within cylinder 34 and the patient's lungs is measured by a pressure transducer 102 which produces a computer input signal 104 proportional to the instantaneous pressure. A position transducer 106 produces a computer input signal 108 proportional to the instantaneous position of piston 98.

Computer 100 contains an adjustable pressure-time waveform generator 110 which is programmed to produce an output signal 112 representing a waveform describing an idealized time-dependent build-up of pressure in the lungs of a normal patient for each inspiratory cycle. The computer is programmed to generate, in response to signal 104 and other programmed information to be described in detail below, an output signal 114 which actuates suitable piston drive means 116, preferably a translational motor, to control the position of reservoir piston 98.

Elapsed time for each inspiratory cycle is computed internally within computer 100 by program logic 118 in response to a data signal 119 from computer 46 representing the patient's respiratory rate and inspiration/expiration ratio. (For reasons of clarity, FIG. 7 shows that signal 119 is generated by rate/ratio data 120 in response to a signal 121 from computer 46. Signal 119 is actually generated by computer 46 in response to rate/- ratio data fed to the computer). Program 118 produces an output signal 122 representing the instantaneous elapsed time, and this signal is fed to an internal logic program 124 within the computer, together with pressure signal 104, to produce an output signal 126 representing a waveform of the actual pressure build-up as a function of time. Actual pressure signal 126 is compared with the ideal pressure-time waveform 112 at a summing point 128 to produce a pressure error signal 130. The pressure error signal is fed to internal program logic 131 to convert the pressure signal to a corresponding piston position error signal 132 representing the displacement of piston 98 required to accommodate the pressure represented by the pressure error signal. Position error signal 132 partially controls movement of reservoir piston 98 via output signal 114.

Thus, if the patient's breathing is normal, error signal 132 will be zero, and pressure within the patient's lungs will be allowed to increase throughout the inspiratory cycle without filling the accommodating reservoir. In this instance, accommodating piston 98 will remain in a fixed position, shown in phantom line in FIG. 6, blocking the flow of gas into the accommodating reservoir. That is, computer output signal 114 instructs the accommodating piston actuating means 116 to hold reservoir piston 98 in its position blocking the accommodating reservoir as long as pressure build-up is normal. Thus, all the gas forced by the primary piston is delivered to the patient as long as the pressure build-up within the system remains normal throughout the inspiratory cycle.

However, if the patient has high airway resistance or lung compliance problems, or if the patient coughs or voluntarily resists gas being delivered to his lungs, pressure in the system exceeds normal and pressure feedback signal 104 will be greater at a given point in time represented by signal 119 than the ideal pressure represented by signal 112. In this instance, the magnitude of pressure error signal 130 becomes greater than zero and instructs the piston drive means 116, via output signal 114, to withdraw reservoir 98 from the position shown in phantom lines in FIG. 7 so as to increase the volume of reservoir 96, thereby lowering the overall pressure in the patient's lungs and the primary piston system. The magnitude of accommodation, i.e., the travel of piston 98 away from zero reservoir volume, is proportional to the magnitude of the inappropriate pressure build-up, and therefore the magnitude of pressure error signal 83. FIG. 7 shows the movement of accommodating piston 98 during excess pressure build-up, where the piston tends to move in the direction of arrows 133 to allow gas which cannot be accepted by the patient to fill the accommodating reservoir.

Computer 100 is also programmed to actuate reservoir piston 98 so it will push back with sufficient force that the entire predetermined volume of gas represented by signal 54 will be forced back into the patient by the end of the inspiratory cycle. To accomplish this result, the position of the reservoir piston throughout inspiration is measured by position transducer 106 which feeds back to computer 100 the signal 108 which is proportional to the displacement of the piston from its reservoir-blocking position. The computer is programmed to instruct translational motor 116 to push back with a force proportional to both the volume of gas in the accommodating reservoir and the elapsed time from the beginning of the inspiratory cycle. Thus, if the excess pressure within the system is relatively small, then the volume of gas within the accommodating reservoir is relatively small, and the accommodating piston will be instructed to push back with a small force sufficient to push the gas in the reservoir back into the patient's lungs by the end of the inspiratory cycle. This movement of piston 98 is represented by arrows 134 shown in FIG. 16.

If excess pressure build-up within the system is relatively large, then the volume of gas within the accommodating reservoir also is large, and output signal 114 will instruct actuator 116 to push back on the reservoir piston with a large force to insure that gas in the reservoir will be delivered to the patient by the end of the cycle.

The force applied by the reservoir piston also is dependent upon the elapsed time during the inspiratory cycle. That is, during the early portion of the cycle the accommodating piston is instructed to push back with a relatively low force. However, as the end of the inspiratory cycle approaches and less time remains to empty the reservoir, output signal 114 instructs the piston actuator 116 to push back harder and harder to insure that the preset volume of gas will be delivered to the patient by the end of the cycle.

Thus, the pressure accommodating system is programmed to receive any gas which initially cannot be accepted by the patient because of abnormalities in his pulmonary system. The gas stored in the accommodating reservoir is pushed back into the patient's lungs during the remaining portion of the inspiratory cycle under such conditions that maximize the chance of accepting the entire preset volume of gas before the end of the cycle. Thus, when excess pressure builds up in the system, the gas is not vented to the atmosphere, but is stored and redelivered under controlled conditions designed to enable the patient to accommodate the desired volume of gas.

FIG. 17 shows the accommodating piston 98 in its desired position at the end of the inspiratory cycle. During the expiratory cycle which follows, the primary piston 32 retracts in the direction of arrows 136 in readiness for the next inspiratory cycle.

The foregoing concepts may be best understood by referring to the graphic displays and waveforms shown in FIGS. 10 through 25 FIG. 10 shows a graphic display of idealized pressure build-up signal 112 compared with actual pressure build-up signal 126. Initially during inspiration error signal 130 builds up to a relatively large magnitude represented at 130a to instruct the reservoir piston 98 to accommodate. Later in inspiration, as the allowable pressure is increased, error signal 130 has a relatively small magnitude represented at 130b. In this situation, the accommodation system has provided pressure accommodation so that the actual pressure in the system at the end of the inspiratory cycle is substantially equal to the desired pressure represented by signal 122.

FIG. 11 shows a graphic representation of actual pressur build-up signal 126 in which the ideal pressure accommodation situation described in FIG. 10 does not occur. In the condition represented by FIG. 11 the pressure in the piston/patient system remains high, and a relatively large pressure error signal 130c early in inspiration remains until the end of the inspiratory cycle, as represented by the error at 130b.

As described above, error signals 130c and 130d are arranged to instruct translational motor 116 to move accommodating piston 98 from left to right in FIG. 7 to increase reservoir volume. However, if this movement of the piston is allowed late in the inspiratory cycle, it creates the undesirble situation where gas would remain in reservoir 96 and deprive the patient of a necessary volume of gas to insure adequate ventilation. To overcome this undesirable situation, computer 100 is programmed to override the pressure accommodation system during the late portion of the inspiratory cycle to insure that the preset volume of gas, represented by signal 54, is delivered to the patient with each breath. The reservoir piston is programmed to return in an optimal manner for the prevailing conditions of reservoir volume and elapsed time of the inspiratory cycle to insure that the patient receives the preset volume under conditions which are safe and comfortable to accommodate.

The override system is best understood by referring to FIG. 7 together with the graphic displays shown in FIGS. 12 through 15 position signal 108 and time signal 122 are both fed to program logic 138 within computer 100 which produces an output signal 140 representing the actual position of reservoir piston 98 at any given time during the inspiratory cycle. Position signal 140 is fed to internal program logic 142 adapted to produce a piston position signal 144 which always instructs the reservoir piston to return to zero by the end of the inspiratory cycle. Preferably, program 142 instructs the piston to return to zero in a substantially asymptotic manner which depends upon the magnitude of position feedback signal 108 and the time remaining (time signal 122) until the end of inspiration. Position signal 144 and pressure accommodate signal 132 are both fed to signal weighting and discrimination means, preferably an alternate time sampling device 146, which alternately allows signal 144 and signal 132 to pass to motor 116 as signal 144, i.e., a composite of signals 132 and 144.

The operation of the signal sampling device 146 is best understood by referring to FIGS. 12 through 15. FIG. 12 shows two conditions under which position signal 108 develops during the early portion of inspiration. If the reservoir volume is relatively small, a small position signal 108a is developed early in inspiration. At an appropriate real time 90a established by time signal 122, a position return command 144a from logic 142 instructs reservoir piston 98 to gradually return to zero volume by the end of the inspiratory cycle. On the other hand, if the reservoir volume is relatively large, a large position signal 108b develops during the early portion of the inspiratory cycle. At an appropriate real time 90b established by time signal 122, a position signal 144b instructs piston 98 to return to zero volume at a faster rate than does position signal 144a.

FIG. 13 shows the operation of program logic 142 for a situation in which a similar reservoir piston displacement occurs during a late portion of the inspiratory cycle. At appropriate real times represented by 90c, 90d program 142 generates position commands 144c and 144d, respectively, to return the accommodating piston to zero volume at a faster rate than was instructed by position commands 144a and 144b, the reason being that there is less time for the same volume to return to zero.

FIGS. 14 and 15 illustrate how signal sampling device 146 attenuates pressure accommodation signal 132 with position signals 144 so as to return the reservoir volume to zero by the end of the inspiratory cycle. FIG. 14 shows how a small pressure accommodation signal is attenuated by periodic position return signals 144e (shown in dotted lines) so that reservoir piston 98 gradually returns to zero volume by the end of inspiration. This volume of gas returned to the patient/piston system is accepted well, without additional pressure build-up, as represented by signal 132e shown in solid lines. A typical pressure-time response of this type is illustrated by curve 126 of FIG. 10.

On the other hand, composite curve 114f, 132f of FIG. 14 illustrates a situation in which gas delivered by main drive piston 32 is not accepted well by the patient, thereby producing a high pressure error signal at the end of inspiration. In this instance, pressure accommodation command 132f instructs piston 98 to accept larger and larger reservoir volumes. As a result, program 142 produces position commands 144f which periodically attenuate signal 132f at a progressively higher rate to insure that reservoir piston 98 will return to zero by the end of inspiration.

Although the reservoir volume return is optimized, there will nevertheless be clinical situations in which pressure build-up produced by composite signal 114 will be excessive for a given patient. This excess pressure is vented to the atmosphere by an adjustable safety relief valve 148 coupled to line 42. The pressure relief valve can be a simple weighted or spring-loaded device, or in a more advanced form can be an electronically, or fluidically, controlled device coupled to pressure input signal 112 to allow pressure venting at the particular time of inspiration.

FIG. 15 illustrates how computer program logic 142 is able to correct for sudden changes in pressure during the inspiratory cycle. A curve for such an inspiratory cycle includes a portion 150 early in inspiration, which is similar to curve 132e, 144e of FIG. 14. That is, initial displacement of piston 98 is relatively small and gas stored in the reservoir is favorably returned to the patient/piston system by piston 98. However, at a time 90e a high pressure problem develops, such as with a cough. The response of program 142 to the high pressure condition is illustrated by a portion 151 of the curve in FIG. 15 which is similar in response to curve 132f, 144f of FIG. 14 Pressure accommodation represented by curve 132f is less than adequate following the high pressure condition, but the piston displacement correction is more forceful, as represented by curves 144f, to insure that the reservoir piston returns to zero position by the end of the inspiratory cycle.

There will sometimes be excessive accommodation situations which the accommodating system described in FIGS. 10 through 15 is unable to manage within the available inspiratory time. This usually arises during a cough, a series of coughs, or when the patient is struggling and breathing out while the respirator is attempting to force air into his lungs. In these instances, it could be dangerous for the respirator to force large volumes of air into the patient's lungs near the end of the inspiratory cycle, since there may be insufficient time to accomplish this task without injuring the patient' lungs.

Accordingly, for excessive accommodation situations, the inspiratory time of the particular cycle is prolonged by modifying the system of FIG. 7 to include an inspiratory prolongation computer 152 shown in FIG. 8. The computer includes a prolongation initiation logic program 153a which receives a position signal 108 from position transducer 106 to instruct the program that the accommodating reservoir piston has moved from its ideal position of zero volume. Program 153a also receives output signal 54 from waveform generator 46 indicating the desired piston position (or volume) for the particular time interval during the inspiratory cycle. Program 153a quantifies the input information received, and when a piston position deviation greater than a predetermined magnitude is exceeded for the particular interval of the inspiratory cycle, a prolongation time logic program 153b is activated to prolong the inspiratory time. A control 153c adjusts the magnitude of the position deviation at which prolongation is triggered.

A position deviation signal 153e is generated by program 153a to activate prolongation time program 153b, the magnitude of signal 153e being proportional to the deviation of the piston from the predetermined allowable deviation. Program logic 153b controls the prolongation time in accordance with the magnitude of the piston position deviation detected by program 153a. For example, as the piston position deviation from the ideal represented by signal 153e increases, program 153b extends prolongation time. Program 153b generates an output 154 which overrides the inspiratory time base signal 54 from waveform generator 46 to extend the inspiratory time for the particular cycle.

The graph shown in FIG. 9 illustrates the function of the inspiratory prolongation override. Piston displacement initially follows a curve 108a until time $t_{c1}$ where an excessive first cough triggers the override system to prolong inspiratory time from the original inspiratory time $t_0$ to time $t_1$. Piston displacement follows curve 108b as the piston recovers and again forces air into the patient's lungs. At time $t_{c2}$ a second excessive cough triggers the override system to extend the length of the inspiratory cycle from time $t_1$ to time $t_2$. The piston displacement then follows curve 108c as the piston recovers and forces air into the patient's lungs until time $t_2$ is reached, at which time the expiratory cycle begins.

Figure 18:
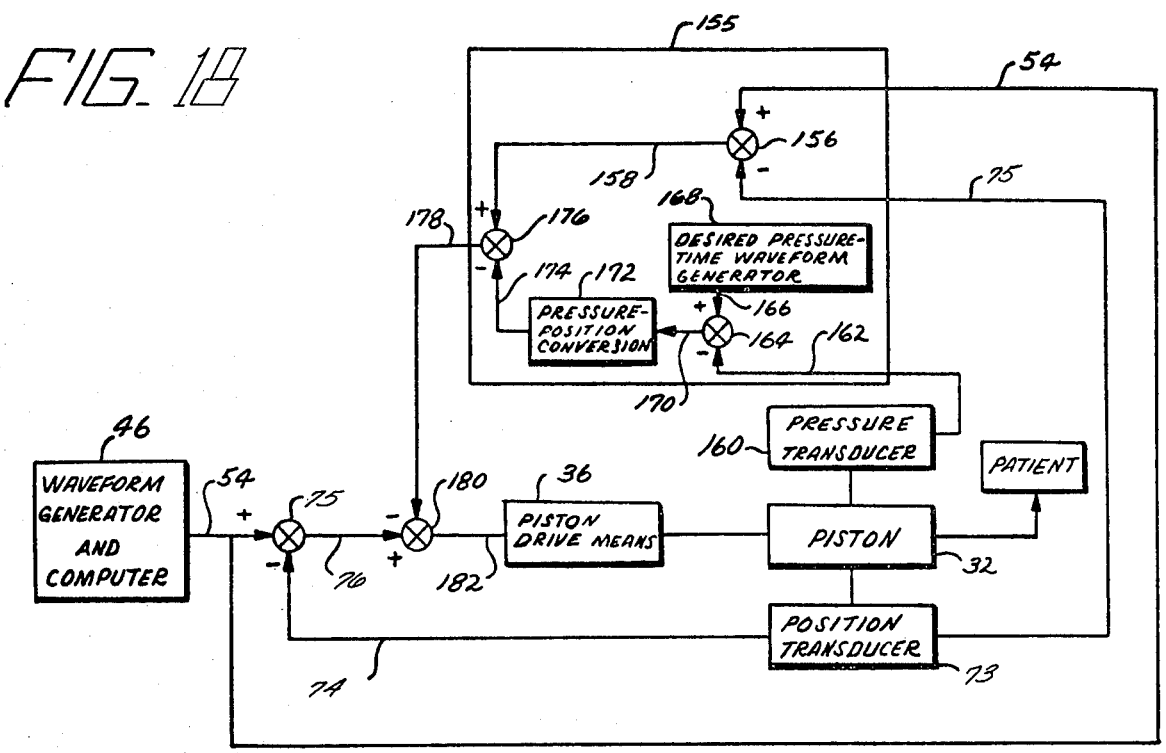
FIG. 18 is a schematic block diagram showing a respirator with an accommodation system in which a piston without an accommodating reservoir is controlled to deliver an optimized volume of gas to a patient during inspiration.

FIG. 18 shows an alternative electrical accommodation system which can be added to the primary piston drive system of FIG. 1 without the need for an accommodating reservoir. As described above, computer output signal 54 represents a desired volume-time waveform which can be adjusted in accordance with the particular physiological condition of each patient's pulmonary system. Signal 54, together with position signal 74 from transducer 73 are fed to a special purpose computer 155 where they are compared at a summing point 156 to produce a position error signal 158. Analog computer 155 performs essentially the same function as computer 100, i.e., it produces accommodation logic in response to pressure accommodation instructions and position accommodation instructions. Pressure accommodation for computer 155 is essentially the same as that described previously for computer 100. That is, a pressure transducer 160 produces an output signal 162 representing the instantaneous pressure within main drive piston 32. Signal 162 is fed to a summing point 164 in computer 155 where it is compared with a desired pressure-time waveform 166 generated by a waveform generator 168, (Preferably, pressure signal 162 is converted to a pressure-time waveform in a manner identical to that previously described for signal 126. However, these steps have been abbreviated in the system shown in FIG. 18) Pressure signals 166 and 162 are compared to produce a pressure error signal 170 which is fed to internal program logic 172 to convert the pressure error signal to a corresponding piston position signal 174 representing the displacement of piston 32 required to correct for the pressure error.

Pressure accommodation signal 174 is compared with volume displacement error signal 158 at a summing point 176 to produce a composite piston position error signal 178 comparable to position error signal 114 described above for the system shown in FIG. 7. Position error signal 178 is weighted in either its pressure component or volume displacement component, in a manner similar to, but not necessarily identical to, the time weighting format provided by sampling device 146 described above. (The sampling device for signals 158 and 174 is not shown in FIG. 18 for brevity.) Composite piston displacement error signal 178 is fed to a summing point 180 where it is compared with the basic piston position error signal 80 to produce an accommodation error signal 182 to drive piston 32.

Thus, if no excessive pressure build-up occurs in piston 32, the waveform represented by signal 182 is substantially identical to the waveform of main position error signal 80, and the piston will operate as described in the system shown in FIG. 1. However, if excessive piston/patient pressure build-up is detected, position signal 178 instructs piston drive means 36 to slow the relative forward progression of piston 32, thus giving time for pressure accommodation. Should the pressure build-up be relatively large, the same logic will either stop, or if necessary, retard the forward motion of piston 32 to provide pressure accommodation. The desired volume-time waveform represented by position signal 54 is continuously compared with actual piston position signal 74 to command the piston drive means 36 to force substantially all the required volume of gas into the patient by the end of the inspiratory cycle. Thus, accommodation is provided by pressure and volume displacement of the unified piston/reservoir system of FIG. 18 in a manner similar to that provided by the separate accommodating reservoir described in the system shown in FIG. 7.

Figure 19:
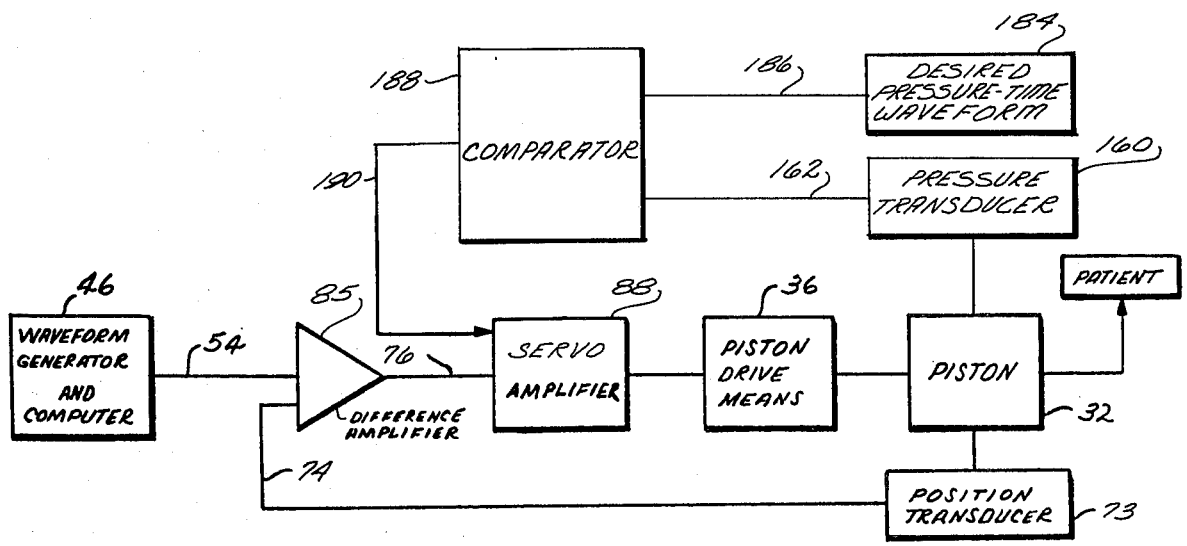
FIG. 19 is a schematic block diagram showing an alternate control system for achieving accommodation using the piston drive system shown in FIG. 18.

FIG. 19 shows an alternate embodiment of the accommodation system described in FIG. 18. Pressure within the reservoir of piston 32 is measured by pressure transducer 160 which in turn produces pressure output signal 162 representing the instantaneous presssure within the piston. A waveform generator 184, which is similar to waveform generator 168, produces an output signal 186 representing a desired time-dependent pressure buildup within the pressure/patient system. A comparator 188 compares signals 162 and 186. If the actual pressure, represented by signal 162, is equal to or greater than the desired pressure, represented by signal 186, then an electrical accommodation signal 190 generated by the comparator is fed to servo amplifier and compensation circuits shown in FIGS. 5 and 6 above, for example. The signal overrides the position information from difference amplifier 190. The override limits the force applied to the piston by drive means 36 so that the piston temporarily lags behind or regresses from the desired volume waveform represented by signal 54, and as the desired maximum pressure increases later in the cycle, the actual volume "catches up" with the desired volume.

Alternately, if the actual pressure is less than the desired pressure, accommodation signal 190 overrides positions signal 82 and commands the piston force to temporarily increase to enable the volume delivered to the patient to catch up with the desired volume.

Thus, as the maximum pressure builds up throughout the inspiratory cycle, the entire volume of gas preset by signal 54 is forced into the patient's lungs before the end of the cycle. The accommodating signal prevents excess pressure from being generated, which increases the chance that the patient will be able to accept the entire preset volume of gas.

Figure 20:
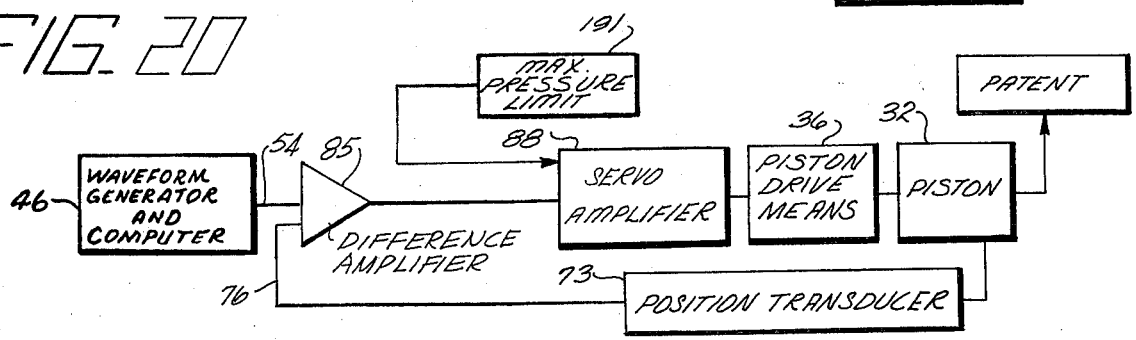
FIG. 20 is a schematic block diagram showing an alternate embodiment of the system shown in FIG. 19.

FIG. 20 shows a presently preferred system for accommodating premature excessive pressure buildup in the patient's lungs during any inspiratory cycle. The system includes a variable maximum pressure limit circuit 191 for producing a pressure override signal which is fed to the servo amplifier and compensation circuits, along with the signal from the difference amplifier 85. The pressure limit circuit 191 includes a maximum pressure limit in the form of a pressure-versus-time waveform representing the change in maximum allowable pressure buildup throughout the inspiratory cycle. Generally speaking, the maximum pressure limit is relatively small early in inspiration, and becomes progressively larger during a later portion of the inspiratory cycle. The maximum pressure buildup waveform can be varied for each patient to accommodate the patient's specific pulmonary problem.

The pressure limit circuit also includes a pressure transducer for monitoring the actual pressure buildup in the patient's lungs throughout the inspiratory cycle. The maximum pressure limit waveform is constantly compared with the actual pressure buildup throughout thee cycle. Whenever the actual pressure in the patient's lungs reaches the maximum pressure limit, the override signal from the pressure limit circuit instructs the respirator piston to stop further increases in the pressure in the patient's lungs. Preferably, the piston responds to the override signal by holding at the maximum allowable pressure until the end of the cycle, with the gas for the remainder of the cycle being forced into the patient's lungs at a reduced flow rate. However, the system can be modified to hold at the maximum pressure limit momentarily until the maximum pressure limit increases by a certain amount, after which the gas flow rate can be increased within the pressure limit dictated by the maximum allowable pressure limit waveform.

FIG. 21 shows a method for modifying the system shown in FIG. 19 to provide prolongation of the inspiratory time for exccessive accommodation problems. The system shown in FIG. 21, and its mode of operation, are substantially identical to that of the override system shown in FIG. 8.

FIGS. 22 and 23 show an alternate accommodating system which includes a mechanically or fluidically controlled variable-sized accommodating reservoir 192. The accommodating reservoir preferably is a bellows 194, or other suitable means, which expands and contracts in response to gas pressure within it.

A spring or series of springs 196 applies a stiff and appropriately variable and adjustable biasing force to the exterior of the expandable accommodating reservoir whih tends to keep the reservoir closed when pressure buildup within the system is below the predetermined amount. If the pressure buildup during the early portion of the inspiratory cycle becomes excessive, gas not accepted by the patient is forced into the accommodating reservoir and causes spring 196 to compress (as shown in FIG. 22), which allows the reservoir to expand and accept the excess volume of gas. As shown in FIG. 23, the biasing force applied by spring 196 tends to push the gas stored in the reservoir back into the patient during the latter portion of the inspiratory cycle. To insure complete emptying of the reservoir at the end of inspiration, a mechanical device (not shown) with sufficient force to overcome any patient resistance is automatically activated during the later portion of the inspiratory phase. If necessary, the spring force 196 is supplemented to insure reservoir emptying. This can be done by a rack and pinion device (not shown) synchronized mechanically with inspiration, but other devices could be used without departing from the scope of this invention.

FIG. 24 shows a preferred embodiment of an "artificial sigh" device 198. As is well known in the art, normal ventilation requires the inspiration of an extra volume of gas, i.e., a sigh, at regular time intervals to supplement the normal tidal volume of gas and prevent the lungs from progressively collapsing. Artificial sigh device 198 simulates a periodic sigh by generating an override to the normal tidal volume of gas delivered by primary piston 32. The device generates a voltage signal 200 representing a sigh volume of gas to be delivered to the patient at specific time intervals controlled by a timer 202. At certain preset time intervals, timer 202 generates a time signal 203 which opens a gate 204 to pass voltage 200 to waveform generator and computer 46. Under normal conditions, computer 46 generates piston drive signal 54 representing the normal tidal volume to be delivered to the patient. However, at the specific time intervals when sigh tidal volume signal 200 is generated, computer 46 generates a signal 205 which activates signal gating means 206, preferably a gate of the exclusive OR type, to cut off signal 54 and substitute a sigh tidal volume displacement signal 208 to apply an extra force to the piston and thereby deliver an extra sigh volume of gas to the patient.

The volume and time reference of the artificial sigh override can be varied relative to the time and volume of the normal waveform represented by signal 54. For example, a larger and slower tidal volume breath may be generated to simulate a periodic sigh. Such a breath is illustrated by the volume-time curve shown in FIG. 25 in which a series of normal volume-time signals 54 are followed by a sigh volume-time signal 208 having both a larger volume and a longer duration, but with the same general shape as the normal volume-time signal.

FIG. 26 shows a more advanced embodiment of the artificial sigh device of FIG. 24. The system shown in FIG. 26 includes a separate sigh computer and waveform generator 210. A timer 212 which determines the number of sigh cycles is adapted to alternately activate either computer 46 or computer 210 to direct either waveform signal 54 or a sigh waveform signal 214, respectively, to signal gating means 216. As described previously for the system of FIG. 24, the signal gating means is a gate of the exclusive OR type which passes either signal 54 or signal 214 to the piston drive means.

Timer 212 is part of an artificial sigh control console 218 which also contains the following controls: a sigh tidal volume control 220 for adjusting the volume of the tidal breath in addition to the added volume of the sigh breath; a control 222 for adjusting the number of sighs that will be delivered during each sigh cycle determined by timer 212; a control 224 which allows adjustment of the length of the inspiratory sigh time which, for example, can be two or three times the length of the normal tidal volume inspiratory time; a manually adjustable control 226 for altering the waveform of the sigh volume-time waveform, which is an important consideration since the volume-time waveform for the sigh volume may have different technical requirements from the volume-time waveform of the normal tidal volume breath; an automatic control 228 for adjusting the sigh volume-time waveform, and which is used as an alternate to the manual adjust control 226; and a control 230 for producing a signal 232 which adjusts the pressure safety limits of relief valve 148. The safety limits established by relief valve 148 generally are distinct from and higher than the venting limits required by the normal tidal volume breath. The pressure limit adjustment could be a fixed pressure venting point operating through relief valve 148 and controlled by mechanical, fluidic, or electrical means. Alternately, the pressure venting could be variable, following a time related pressure build-up during inspiration, as represented by curve 60 in FIG. 2, for example, but in which the relief valve is adjusted to vent at a variable higher level of pressure than the normal pressure generated by normal tidal volume breaths.

FIG. 27 shows a typical volume-time waveform represented by the signal fed to the piston drive means by signal gating means 216. Normal tidal volume breaths 54 are interrupted by sigh volume breath 214a and a different pair of sigh volume breaths 214b. The sigh volume breaths 214a and 214b differ from each other in their volume, waveform shape, inspiration length, and number of breaths per cycle in accordance with the adjustments of the parameters in control console 218.

We claim:
1. A volume-cycled respirator system for delivering a controlled volume of gas to a patient, the system comprising:
   a. displaceable gas delivery means having a position which is adjustable for forcing periodically a volume of gas under pressure into the lungs of a patient throughout an inspiratory period of a respiratory cycle;
   b. drive means operatively connected to the gas delivery means to displace the volume of gas to be delivered;
   c. means for generating a reference signal representing variations in the position of the gas delivery means with respect to time throughout the inspiratory period necessary to deliver a desired volume of gas in accordance with a desired volume-versus-time waveform; and
   d. closed loop feedback means for controlling the instantaneous position of the gas delivery means throughout the inspiratory period, the closed loop feedback means including
      1. first means responsive to the actual position of the gas delivery means for generating a position feedback signal representing the actual volume of gas displaced by the gas delivery means with respect to time throughout the inspiratory period,
      2. second means responsive to said reference signal and said position feedback signal for providing throughout the inspiratory period a position error signal representing the deviation between the instantaneous desired position and the corresponding actual position of the gas delivery means, and
      3. third means for applying said position error signal to the drive means for adjusting the instantaneous position of the gas delivery means in proportion to said error signal throughout the inspiratory period to deliver gas to the patient in accordance with the desired volume-versus-time waveform.

2. A respirator system according to claim 1 in which the gas delivery means comprises a cylinder-and-piston device, and the drive means comprises a translational motor to which the position error signal is applied for causing linear relative motion between the piston and the cylinder.

3. A respirator system according to claim 2 in which the reference signal indicates the desired position of the piston in the cylinder throughout the inspiratory period, and the first means of the closed loop feedback means comprises a position transducer for continuously sensing the actual position of the piston in the cylinder and for producing said position feedback signal, and the second means comprises means for continuously comparing the position feedback signal and the reference signal to generate the position error signal.

4. A respirator system according to claim 3 in which the magnitude and polarity of the position error signal applied to the translational motor are governed by the amount of force and direction of application of the force applied to the piston by the motor to maintain the desired volume-versus-time waveform.

5. A respirator system according to claim 3 in which the translational motor comprises a permanent magnet d.c. motor.

6. A respirator system according to claim 5 in which the position transducer comprises a linear variable-differential transformer.

7. A respirator system according to claim 1 including means for sensing the actual build-up of gas pressure in the patient during gas delivery, means for producing an output representative of a desired gas pressure build-up, means for producing a pressure error signal representing a comparison of the sensed pressure build-up with the desired pressure build-up, and volume adjusting means responsive to the pressure error signal for adjusting the time-dependent volume of gas delivered to the patient by the gas delivery means.

8. A respirator system according to claim 7 including a waveform generator defining an allowable maximum pressure-versus-time waveform for the patient during the inspiratory cycle, and means for generating said pressure error signal to represent the difference between the maximum allowable pressure build-up and the actual pressure build-up.

9. A respirator system according to claim 7 in which the means for sensing pressure build-up comprises a pressure transducer which generates an output signal representing the actual pressure build-up in the patient during the inspiratory cycle, and including a waveform generator defining a pressure-versus-time wavveform defining a maximum allowable pressure build-up throughout a given inspiratory cycle, and means for generating said pressure error signal to represent the difference between the sensed pressure build-up and the maximum allowable pressure build-up.

10. A respirator system according to claim 7 in which the means for generating the desired pressure build-up comprises a pressure-versus-time waveform representing the maximum allowable pressure build-up throughout the inspiratory cycle.

11. A respirator system according to claim 10 in which the volume-adjusting means adjusts the position of the gas delivery means throughout the inspiratory period to hold the actual pressure in the patient at the maximum allowable pressure at any instant when the actual pressure reaches the maximum allowable pressure limit.

12. A respirator system according to claim 11 including means for holding the actual pressure generated by the gas delivery means at a constant hold pressure for the remainder of the inspiratory cycle when the actual pressure reaches the maximum allowable pressure limit.

13. A respirator system according to claim 1 including means for intermittently providing an overriding command to deliver a volume of gas representing a sigh volume which differs from the volume of gas required normally during the inspiration period, the sigh volume being defined by an output command signal representing the time-varying position of the gas delivery means necessary to displace a desired sigh volume of gas in accordance with a desired sigh volume-versus-time waveform, and means for varying the shape of the sigh volume-versus-time waveform independently of the volume-versus-time waveform associated with normal, sigh-absent respiration.

14. A respirator system according to claim 1 in which the gas delivery means comprises a chamber containing gas to be delivered to the patient, a conduit extending between the chamber and the patient, a piston movable only in a first portion of the chamber to force gas from the chamber through the conduit to the patient in accordance with the position error signal, the chamber also including a second portion in gas communication with the first portion for receiving the volume of gas which is forced by the piston but is not accepted by the patient, and means operative separately from the piston for forcing the gas out of the second portion of the chamber through the conduit to the patient.

15. A respirator system according to claim 14 including means for sensing pressure build-up in the lungs off the patient in response to the gas delivered by the piston, and means for adjusting the time-dependent volume of gas forced out of the second portion of the chamber in accordance with the sensed pressure build-up.

16. A respirator system according to claim 1 including means for varying the reference signal with respect to time to provide a selected volume-versus-time waveform, and in which the reference signal generating means generates said selected reference signal throughout the inspiratory period.

17. A volume-cycled respirator system for delivering a controlled volume of gas to a patient, the system comprising:
  a. linearly displaceable gas delivery means having a position which is adjustable for forcing periodically a volume of gas under pressure into the lungs of a patient throughout an inspiratory period of a respiratory cycle;
  b. a translational motor having an input for being converted into translational motion of an output shaft of the motor for linearly positioning the gas delivery means to displace the volume of gas to be delivered;
  c. means for generating a reference signal representing variations in the position of the gas delivery means with respect to time throughout the inspiratory period necessary to deliver a desired volume of gas in accordance with a desired volume-versus-time waveform; and
  d. closed loop feedback means for controlling the position of the gas delivery means throughout the inspiratory period, the closed loop feedback means including
    1. a position transducer responsive to the actual position of the gas delivery means to produce a position feedback signal representing the actual volume of gas displaced by the gas delivery means with respect to time throughout the inspiratory period,
    2. means for comparing said reference signal with said position feedback signal to produce throughout the inspiratory period a position error signal representing the deviation between the instantaneous desired position and the corresponding actual position of the gas delivery means, and
    3. means for applying said position error signal to the input of the translational motor for adjusting the instantaneous position of the gas delivery means in proportion to said error signal throughout the inspiratory period to deliver gas to the patient in accordance with the desired volume-versus-time waveform.

18. A respirator system according to claim 17 in which the feedback means further includes a pressure transducer for sensing the build-up of gas pressure in the patient during the inspiratory cycle; means for comparing the sensed pressure build-up with an allowable pressure build-up to generate a pressure error signal representing excessive pressure buld-up; and means responsive to the pressure error for adjusting the volume of gas displaced by the gas delivery means.

19. A respirator system according to claim 17 in which the magnitude of the position error signal is proportional to the distance through which the gas delivery means is to be displaced, and the polarity of the said signal is determined by the direction in which the gas delivery means is to be displaced to maintain the desired volume-versus-time waveform.

20. A respirator system according to claim 17 in which the gas delivery means comprises a cylinder-and-piston device; and in which the translational motor causes linear relative motion between the piston and the cylinder.

21. A respirator system according to claim 20 in which the translational motor comprises a permanent magnet d.c. motor.

22. A respirator system according to claim 21 in which the position transducer comprises a linear variable-differential transformer.

23. A respirator system according to claim 21 in which the magnitude and polarity of the position error signal applied to the translational motor are governed by the amount of force and direction of application of the force applied to the piston by the translational motor to maintain the desired volume-versus-time waveform.

24. A respirator system according to claim 21 including means for varying the reference signal with respect to time to provide a selected volume-versus-time waveform, and in which the reference signal generating means generates said selected reference signal throughout the inspiratory period.

25. A respirator system according to claim 17 including means for varying the reference signal with respect to time to provide a selected volume-versus-time waveform, and in which the reference signal generating means generates said selected reference signal throughout the inspiratory period.

26. A method for delivering a controlled volume of gas to a patient from a displaceable gas delivery means for forcing periodically a volume of gas under pressure into the lungs of the patient throughout an inspiratory period of a respiratory cycle, in which the cycling of the gas delivery means is controlled by drive means for positioning the gas delivery means to displace the volume of gas delivered to the patient, the method comprising the step of:
- a. generating a reference signal representing variations in the position of the gas delivery means with respect to time throughout the inspiratory period necessary to deliver a desired volume of gas to the patient in accordance with a desired volume-versus-time waveform;
- b. sensing throughout the inspiratory period the instantaneous actual position of the gas delivery means;
- c. generating, in response to said sensed instantaneous position, a position feedback signal representing the actual volume of gas displaced by the gas delivery means throughout the inspiratory period;
- d. generating, in response to said reference signal and said position feedback signal, a position error signal representing the deviation between the instantaneous desired position and the corresponding actual position of the gas delivery means throughout the inspiratory period; and
- e. applying the error signal to the drive means to adjust the instantaneous position of the gas delivery means in proportion to said error signal to deliver gas to the patient throughout the inspiratory period in accordance with the desired volume-versus-time waveform.

27. The method according to claim 26 in which the gas delivery means is a linearly displaceable piston-and-cylinder device, and the drive means is a translational motor; and including the step of adjusting the linear position of the piston-and-cylinder device by applying the error signal to the translational motor for converting the error signal directly into translational motion of a motor output shaft connected to the piston-and-cylinder device to displace the volume of gas to be delivered.

28. The method according to claim 27 including selecting a given reference signal representing a selected volume-versus-time waveform, and generating said selected reference signal throughout the inspiratory period.

29. The method according to claim 26 including selecting a given reference signal representing a selected volume-versus-time waveform, and generating said selected reference signal throughout the inspiratory period.

* * * * *

UNITED STATES PATENT AND TRADEMARK OFFICE
CERTIFICATE OF CORRECTION

PATENT NO. : 4,036,221

DATED : July 19, 1977

INVENTOR(S) : HILLSMAN ET AL

It is certified that error appears in the above-identified patent and that said Letters Patent are hereby corrected as shown below:

Col. 3, line 17, "of" should read -- or --;
         line 25, "one" should read -- One --.

Col. 5, line 53, "inspria-" should read -- inspira- --.

Col. 7, line 28, "each" should read -- such --;
         line 35, "releif" should read -- relief --.

Col.12, line 45, "25" should read -- 15 --;
         line 57, "122" should read -- 112 --;
         line 59, "pressur" should read -- pressure --;
         line 65, "130b" should read -- 130d --.

Col.13, line  3, "undesirble" should read -- undesirable --;
         line 19, "15 position" should read -- 15. Postion --;
         line 32, "accommodate" should read -- accommodation --;
         line 36, "signal 144" should read -- signal 114 --.

Col.17, line 25, "thee" should read -- the --;
         line 41, "exccessive" should read -- excessive --;
         line 54, "whih" should read -- which --.

Col.20, line 48, "wavveform" should read -- waveform --.

Col.21, line 30, "off" should read -- of --.

Signed and Sealed this

Twenty-second Day of August 1978

[SEAL]

Attest:

RUTH C. MASON
Attesting Officer

DONALD W. BANNER
Commissioner of Patents and Trademarks